(12) United States Patent
Nuziard

(10) Patent No.: US 11,806,301 B1
(45) Date of Patent: Nov. 7, 2023

(54) REGENERATING CAVERNOUS TISSUE TO REVERSE SEXUAL DISFUNCTION

(71) Applicant: Jeffrey Nuziard, Colleyville, TX (US)

(72) Inventor: Jeffrey Nuziard, Colleyville, TX (US)

( * ) Notice: Subject to any disclaimer, the term of this patent is extended or adjusted under 35 U.S.C. 154(b) by 0 days.

(21) Appl. No.: 17/901,571

(22) Filed: Sep. 1, 2022

(51) Int. Cl.
*A61H 3/00* (2006.01)
*A61N 5/06* (2006.01)
*A61N 5/067* (2006.01)
*A61B 18/22* (2006.01)
*A61H 23/00* (2006.01)

(52) U.S. Cl.
CPC ........... *A61H 23/008* (2013.01); *A61B 18/22* (2013.01); *A61N 5/067* (2021.08); *A61N 5/0613* (2013.01); *A61H 2205/087* (2013.01)

(58) Field of Classification Search
CPC ... A61H 23/008; A61H 2205/087; A61F 5/41; A61N 5/067; A61N 5/061; A61N 5/0611; A61N 5/0616; A61N 5/0603; A61B 18/20; A61B 2018/00517; A61B 2018/00559
See application file for complete search history.

(56) References Cited

U.S. PATENT DOCUMENTS

| | | | | |
|---|---|---|---|---|
| 8,961,577 B2 * | 2/2015 | Reil | ....................... | A61K 33/26 607/88 |
| 11,564,861 B1 * | 1/2023 | Gaines | .................. | A61H 23/04 |
| 2006/0052847 A1 * | 3/2006 | Davenport | ........... | A61B 18/203 607/88 |
| 2008/0146970 A1 * | 6/2008 | Litman | ..................... | A61N 7/02 601/2 |
| 2009/0024192 A1 * | 1/2009 | Mulholland | ....... | A61B 18/1477 607/99 |
| 2011/0015621 A1 * | 1/2011 | Kreindel | .............. | A61B 18/203 606/14 |
| 2015/0367142 A1 * | 12/2015 | Kazic | ................... | A61N 5/0603 607/89 |
| 2018/0325959 A1 * | 11/2018 | Ichim | ................... | A61K 9/0034 |
| 2019/0030356 A1 * | 1/2019 | Schwarz | .............. | A61H 23/008 |

OTHER PUBLICATIONS

"How Does REGENmax® Improve Sexual Wellness in Men and Women?" Aug. 31, 2021 https://swcoftexas.com/health-and-wellness-blog/how-does-regenmax-improve-sexual-wellness-in-men-and-women (Year: 2021).*
"What to Know About the O-Shot" By Erica Cirino on Nov. 24, 2019 https://www.healthline.com/health/o-shot (Year: 2019).*
"What to Know About the P-Shot" By Tim Jewell, Candice Abellon on Jan. 10, 2020 https://www.healthline.com/health/mens-health/p-shot#takeaway (Year: 2020).*
Lukac et al., "New Skin Treatment Possibilities with Piano Mode on an Nd:YAG Laser" Journal of the Laser and Health Academy, vol. 2011, No. 1; pp. 22-32. Accepted: Mar. 30, 2011. (Year: 2011).*

* cited by examiner

*Primary Examiner* — Boniface Ngathi
(74) *Attorney, Agent, or Firm* — Culhane Meadows PLLC; Robert C. Klinger

(57) ABSTRACT

A treatment that regenerates cells, remodels collagen, and reverses atrophy to restore full sexual function of human genitalia.

11 Claims, 3 Drawing Sheets

REGENERATING CAVERNOUS TISSUE TO REVERSE SEXUAL DISFUNCTION

TECHNICAL FIELD

The present subject matter relates to treating and reversing sexual disfunction in male and female humans.

BACKGROUND

Erectile dysfunction (ED) effects 7 out of 10 men at age 50, and 9 out of 10 at age 75. The first symptoms of ED usually start with the venous leak (trouble sustaining an erection, also known as venogenic ED) and progresses to being able to obtain a 75% erection and continue until complete impotence and atrophy have set in. For many years science has tried to solve erectile dysfunction with pharmaceuticals. While pharmaceuticals, such as PDE5 inhibitors, may lend a temporary effect in giving an erection, they do not address the root causes of erectile dysfunction. Many men have reported a type of resistance to these PDE5 inhibitors after 2-4 years of use.

Women also have sexual disfunction due to degeneration dot their respective genitalia.

BRIEF DESCRIPTION OF THE DRAWINGS

The drawing figures depict one or more implementations, by way of example only, not by way of limitations. In the figures, like reference numerals refer to the same or similar elements.

Features of the various implementations disclosed will he readily understood from the following detailed description, in which reference is made to the appended drawing figures. A reference numeral is used with each element in the description and throughout the several views of the drawing. When a plurality of similar elements is present, a single reference numeral may be assigned to like elements, with an added letter referring to a specific element.

Figure 1:
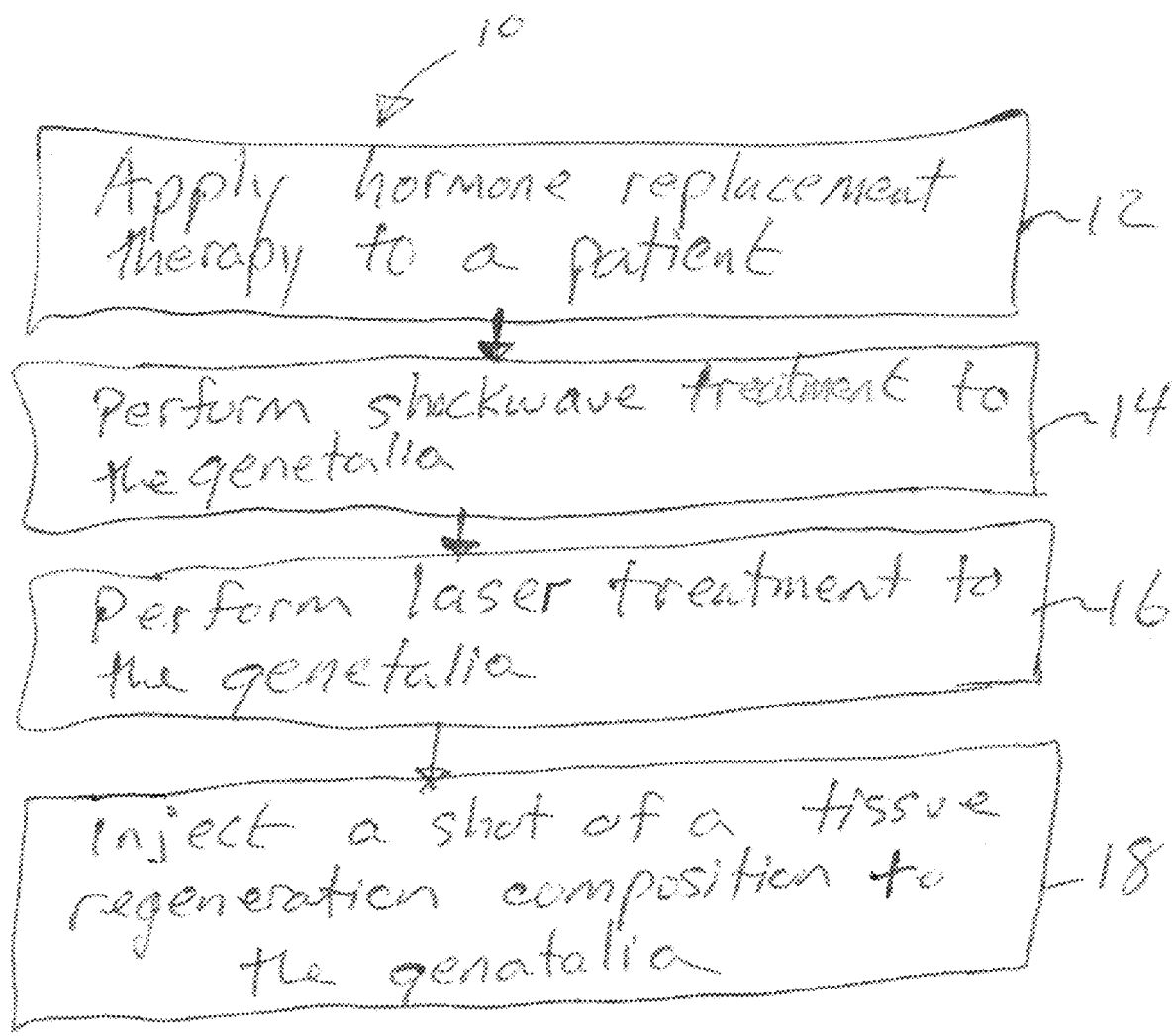
Figure 2:
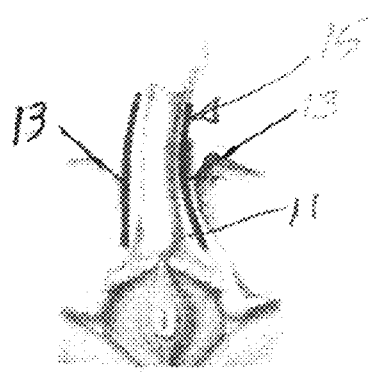
Figure 3:
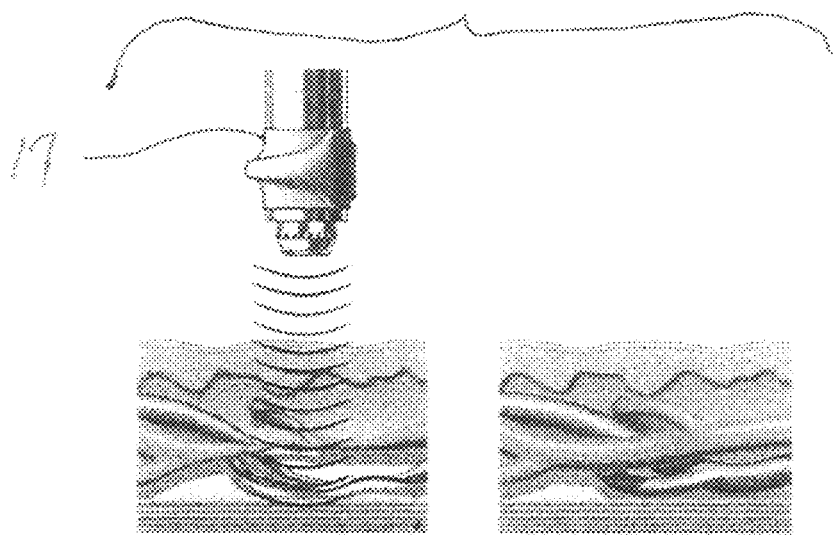
Figure 4:
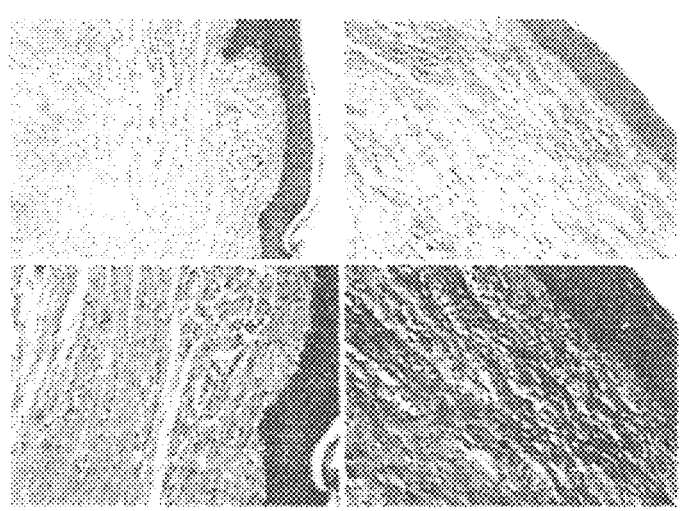
Figure 5:
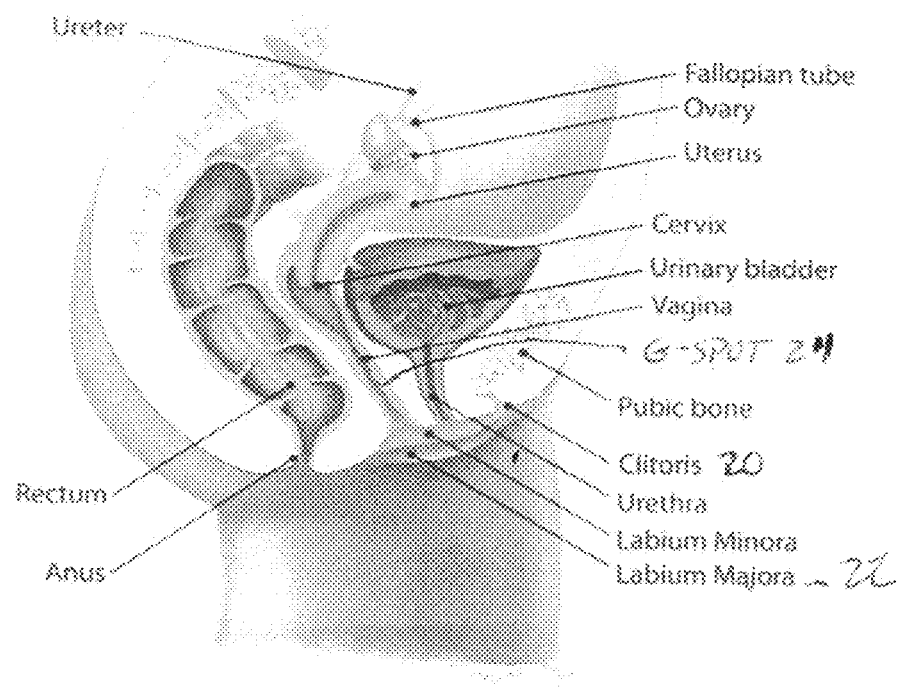

The various elements shown in the figures are of drawn to scale unless otherwise indicated. The dimensions of the various elements may be enlarged or reduced in the interest of clarity. The several figures depict one or more implementations and are presented by way of example only and should not be construed as limiting. Included in the drawing are the following figures:

FIG. 1 is a method of a REGENmax® protocol;

FIG. 2 illustrates each side of the penis shaft covering the entire corpus cavernosum treated with a shockwave treatment;

FIG. 3 illustrates an acoustic shockwave device applied to a male penis to perform the shockwave treatment;

FIG. 4 illustrates creating a neo-collagenesis inside the cavernous tissue using the acoustic shockwave therapy; and FIG. 5 illustrates the female genitalia that receives the REGENmax® protocol.

DETAILED DESCRIPTION

A treatment regenerates cells, remodels collagen, and reverses atrophy to restore full sexual function of human genitalia. The treatment includes administering hormone regenerative therapy (HRT) to the patient, administering acoustic shockwave therapy to the genitalia to generate new vascularity in the genitalia, administering a laser treatment to the genitalia and administering a shot of a tissue regeneration composition to the genitalia to regenerate tissue.

The following detailed description includes systems, methods, techniques, instruction sequences, and computing machine program products illustrative of examples set it in the disclosure. Numerous details and examples are included for the purpose of providing a thorough understanding of the disclosed subject matter and its relevant teachings. Those skilled in the relevant art, however, may understand how to apply the relevant teachings without such details. Aspects of the disclosed subject matter are not limited to the specific devices, systems, and method described because the relevant teachings can be applied or practice in a variety of ways. The terminology and nomenclature used herein is for the purpose of describing particular aspects only and is not intended to be limiting. In general, well-known instruction instances, protocols, structures and techniques are not necessarily shown in detail.

The terms "coupled" or "connected" as used herein refer to any logical, optical, physical, or electrical connection, including a link or the like by which the electrical or magnetic signals produced or supplied by one system element are imparted to another coupled or connected system element. Unless described otherwise, coupled or connected elements or devices are not necessarily directly connected to one another and may be separated by intermediate components, elements, or communication media, one or more of which may modify, manipulate, or carry the electrical signals. The term "on " means directly supported by an element or indirectly supported by the element through another element that is integrated into or supported by the element.

The term "proximal" is used to describe an item or part of an item that is situated near, adjacent, or next to an object or person; or that is closer relative to other parts of the item, which may be described as "distal." For example, the end of an item nearest an object may be referred to as the proximal end, whereas the generally opposing end may be referred to as the distal end.

The orientations of the eyewear device, other mobile devices, associated components and any other devices incorporating a camera, an inertial measurement unit, or both such as shown in any of the drawings, are given by way of example only, for illustration and discussion purposes. In operation, the eyewear device may he oriented in any other direction suitable to the particular application of the eyewear device; for example, up, down, sideways, or any other orientation. Also, to the extent used herein any directional term, such as front, rear, inward, outward, toward, left, right, lateral, longitudinal, up, down, upper, lower, top, bottom, side, horizontal, vertical, and diagonal are used by way of example only, and are not limiting as to the direction or orientation of any camera or inertial measurement unit as constructed or as otherwise described herein.

Additional objects, advantages and novel features of the examples will be set forth in part in the following description, and in part will become apparent to those skilled in the art upon examination of the following and the accompanying drawings or may be learned by production or operation of the examples. The objects and advantages of the present subject matter may be realized and attained by means of the methodologies, instrumentalities and combinations particularly pointed out in the appended claims.

Reference now is made in detail to the examples illustrated in the accompanying drawings and discussed below.

There is a direct correlation of sustained low testosterone causing a degenerative effect to the collagen in the cavernous tissue and the smooth muscle cells (SMC) and the tunica albuginea of the penis. Furthermore, atherosclerosis of the penile vessels that occurs with ageing causes a decrease in penile oxygen tension. This correlation applies to female genitalia as well.

The decrease in penile elasticity and compliance are explained by he changes in the ratio of penile collagen that occur with aging. Contrary to the common view that testosterone deficiency or replacement only effects sexual desire, it also causes penile atrophy. There is a correlation between testosterone deficiency, cavernosal fibrosis, and ED. This disclosure details a multi-modality protocol referred to by applicant as REGENmax® that restores functionality and reverses penile fibrosis and atrophy. The REGENmax® protocol also restores functionality of female genitalia.

The REGENmax® protocol is shown at 10 in FIG. 1. This protocol is applicable to both the male and female genitalia. A process is first described for treating the male penis, and then for treating the female clitoris, labium majora, and the Gräfenberg spot, commonly referred to as the G-spot and which is part of the clitoral network.

At block 12, a complete hormone and blood panel is obtained On a male patient. Then, an appropriate dose of testosterone pellets is administered related to the testosterone deficiency, referred to as hormone replacement therapy (HRT). In an example, patients with lab results being below 500 total testosterone are raised to between 900 and 1100 through HRT.

At block 14, in the same session, the trans dermis 13 on each side of the penis shaft 15 covering the entire corpus cavernosum 11 as shown in FIG. 2 is treated with a shockwave treatment at the time of the blood panel. In an example, the shockwave treatment includes a GAINSwave protocol using an acoustic shockwave device 17 as shown in FIG. 3, such as a device available from Storz Medical AG of Switzerland. In an example, power of the acoustic shockwave device 17 has a power setting of 3.6, at a frequency of 10 Hz. The trans dermis 13 on each side of the penis shaft 15 covering the entire corpus cavernosum 11 is pulsed 2000 times, with 1000 pulses on the dorsal side, and 500 pulses on each side of the internal bulb of the penis 15. This treatment aides in the creation of new vascularity, as well as micro tears in the cavernous tissue and smooth muscle cells (SMC) which yield a cellular regeneration of the tissue. The GAINSwave therapy protocol creates microtraumas in the tissue stimulating a cascade of immune responses. This cascade of immune responses treats the underlying cause of erectile disfunction by stimulating nitric oxide production leading to increased blood flow to the penis 15, breaks up microplaques in the small blood vessels of the penis 15, stimulates angiogenesis, the development of new blood vessels, and stimulating neurogenesis the formation of new nerve tissue for improved sensitivity.

At block 16, a laser 19 is then applied to the penis 15, such as using a SP Dynamis Pro Nd:YAG laser available from Fotono of Dallas, Texas, using a 9 mm spot size, 180 j/cm$^2$, 8 second pulse duration, and a painting technique. The practitioner pulls the penis 15 taught, then paints 4 minutes on each side of the external penis covering the corpus cavernosum 11. This process heats the internal tissue of the penis 15 to approximately 60° C. creating a neo-collagenesis inside the cavernous tissue as illustrated in FIG. 4.

At block 18, a shot of HEshot® available, from the Sexual Wellness Center of Texas, Frisco, Texas, the Applicant of this application, is injected into the penis 15. The HEshot® is based on Cytosomes® available from Neobiosis Labratories of Gainsville, Florida. The application of the HEshot® to the male penis 15 according to this disclosure is a novel treatment to treat sexual disfunction of the male genitalia. A SHEshot®, also available from the Sexual Wellness Center of Texas, is applied to the genitalia of women as shown in FIG. 5. In an example, the HEshot® only needs to be given one time, either at the time of the GAINSwave therapy, or a period thereafter such as 2 weeks. In an example, the HEshot® is administered using a 1 ml syringe with a 31 g needle. 1 ml of HEshot® is drawn and .5 ml is injected into the corpus cavernosum 11 at a 45° angle into the mid shaft on each side of the penis 15. The HEshot® is 10 times more regenerative than Platelet-rich plasma (PRP), and it works at the molecular and cellular level to regenerate new tissue in the genitalia.

In an example, the REGENmax® protocol 10 includes treatments that continue every other week 6-8 times. At that point, a period of six weeks is given as a regeneration time. The REGENmax® protocol 10 treatments then continue for another 6-8 times every other week. Verbal evaluations are taken at each treatment. The HRT continues every 16 weeks with new labs and continued pellet therapy.

STUDY

In a study, 50 males ages 49-75 were treated consistently over one year with the REGENmax® protocol 10. Of the 50 men, 10 were type II diabetics (controlled by medication and diet) and all 50 reporting ED for at least a year or more. Patients 62 and younger are defined as YA (younger age) and patients 65 and older are defined as OA (older age). The severity of ED was rated using a number system 1-5, 1 being severe and 5 being mild. Of the OA patients, 2 of the 29 were rated a 1, 12 were rated 2-3, 12 rated 3-4, and 3 were rated a 5. Of the 21 YA patients, 1 rated a 1, and 20 rated 3-5. The ratings were based on questions, on subject ability to achieve and maintain erection sufficient for intercourse and sustain to desired orgasm. These questions were answered were by the patients prior to the treatments beginning.

After one year of treatments, 47 of the 50 patients regained enough of an erection (80% or more) for penetration and sustainability to desired orgasm. The YA patients achieved results after the initial 6-8 treatments yet continued through the entire year. The OA patients obtained the same results, on average, after 15 treatments. All patients reported a firming of the penis in the flaccid state. The 3 patients that did not obtain desired results achieved less than a 50% of an erection, were all three diabetics and two were smokers of over a pack a day.

With respect to treating females with issues including sexual disfunction, the REGENMax® protocol 10 using the SHEshot® is administered to the female genitalia including the clitoris 20, the labium majora 22, and the G-Spot 24 as shown FIG. 5.

The REGENmax® protocol 10 is done in the same order and using the same techniques used with men. The laser procedure is done intra-vaginally for all atrophy, incontinence, and vaginal tightness issues as well as extra-vaginally for labia regeneration and uses Fotona's Er:YAG wavelength laser. The GAINSwave procedure is done trans clitoral, and the SHEshot® is injected .5 ml into the clitoris 20 and .5 ml into the G-spot 24. HRT is done on women as well.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises, " "comprising," "includes," "including," or any other variation thereof, are intended to cover a non-exclusive inclusion, such that a process, method, article, or apparatus that comprises or includes list of elements or steps does not include only those elements or steps but may include other elements or steps not expressly listed or inherent to such process, method, article, or apparatus. An element preceded by "a" or "an" does not, without further constraints, preclude the existence of additional identical elements in the process, method, article, or apparatus that comprises the element.

Unless otherwise stated, all measurements, values, ratings, positions, magnitudes, sizes, and other specifications that are set forth in this specification, including in the claims that follow, are approximate, not exact. Such amounts are intended to have a reasonable range that is consistent with the functions to which they relate and with what is customary in the art to which they pertain. For example, unless expressly stated otherwise, a parameter value or the like may vary by as much as 10% from the stated amount.

In addition, in the foregoing Detailed Description, various features are grouped together in various examples for the purpose of streamlining the disclosure. This method of disclosure is not to be interpreted as reflecting an intention that the claimed examples require more features than are expressly recited in each claim. Rather, as the following claims reflect, the subject matter to be protected lies in less than all features of any single disclosed example. Thus, the following claims are hereby incorporated into the Detailed Description, with each claim standing on its own as a separately claimed subject matter.

While the foregoing has described what are considered to be the best mode and other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

What is claimed is:

1. A method of treating sexual disfunction of genitalia of a human patient, comprising:
   administering hormone regenerative therapy (HRT) to the patient;
   administering accoustic shockwave therapy to the genitalia to generate new vascularity in the genitalia;
   administering a laser treatment to the genitalia using an neodymium-doped yttrium aluminum garnet (Nd: YAG) laser pulsed with a 8 second pulse duration, 9 mm spot size, 180 J/cm$^2$, for 4 minutes on each side of the genitalia, the laser treatment generating non-ablative thermal energy to heat internal tissue of the genitalia to 60 degrees Celsius, and remodel collagen in the genitalia without mechanical stimulation; and
   administering a shot of a tissue regeneration composition to the genitalia to regenerate tissue.

2. The method as specified in claim 1, wherein the laser treatment uses a painting technique.

3. The method as specified in claim 1, wherein the shockwave therapy generates micro tears in cavernous tissue and smooth muscle cells (SMC) to yield a cellular regeneration of the tissue.

4. The method as specified in claim 3, wherein a trans dermis on each side of a penis shall covering a corpus cavernosum is treated with the shockwave therapy.

5. The method as specified in claim 1, wherein the laser treatment creates a neo-collagenesis inside cavernous tissue of the genitalia.

6. The method as specified in claim 1, wherein a dermis of female genitalia is administered the shot.

7. The method as specified in claim 6, wherein a dermis of a clitoris is treated with the shockwave therapy.

8. The method as specified in claim 6, wherein a dermis of a Gräfenberg spot is treated with the shockwave therapy.

9. The method as specified in claim 6, wherein a dermis of a labia majora is treated with the shockwave therapy.

10. A method of treating sexual disfunction of a penis of a male human patient, comprising:
    administering hormone regenerative therapy (HRT) to the patient;
    administering accoustic shockwave therapy to the penis of the patient to generate micro tears in cavernous tissue and smooth muscle cells (SMC), creating cellular regeneration of the cavernous tissue and generating new vascularity in the penis;
    administering a laser treatment to the penis using an neodymium-doped yttrium aluminum garnet (Nd: YAG) laser pulsed with a 8 second pulse duration on each side of the penis, 9 mm spot size, 180 J/cm$^2$, for 4 minutes on each side of the penis, the laser treatment generating non-ablative thermal energy to heat internal tissue inside the penis, and remodel collagen in the penis without mechanical stimulation to create neo-collagenesis inside cavernous tissue of the penis; and
    administering a tissue regeneration composition to the penis to regenerate the cavernous tissue.

11. The method as specified in claim 10, wherein a trans dermis on each side of the penis covering a corpus cavernosum is treated with the shockwave therapy.

* * * * *